United States Patent [19]

Evrard et al.

[11] Patent Number: 4,490,497

[45] Date of Patent: Dec. 25, 1984

[54] COMPOSITIONS FOR SURGICAL CEMENT, BASED ON AT LEAST ONE ACRYLIC MONOMER AND AT LEAST ONE ACRYLIC POLYMER

[75] Inventors: Paul Evrard, Fourqueux; Michel Lahille, Vauhallan; Michel Avenel, Gisors, all of France

[73] Assignees: Altulor S.A.; C.L.L. S.A.R.L., both of France

[21] Appl. No.: 443,628

[22] Filed: Nov. 22, 1982

[30] Foreign Application Priority Data

Nov. 20, 1981 [FR] France .................. 81 21732

[51] Int. Cl.³ .................. A61K 6/08; C08K 5/13
[52] U.S. Cl. .................. 524/349; 156/327; 424/81; 427/207.1; 523/116; 525/193; 525/194; 525/263; 525/273; 525/304; 525/309
[58] Field of Search .................. 524/349; 523/116; 424/81; 525/193, 194, 263, 273, 304, 309

[56] References Cited

U.S. PATENT DOCUMENTS 3,880,803  4/1975  Keizer .................. 524/349
4,341,691  7/1982  Anuta .................. 523/116

*Primary Examiner*—Jacob Ziegler
*Attorney, Agent, or Firm*—Finnegan, Henderson, Farabow, Garrett & Dunner

[57] ABSTRACT

A component system for surgical cement, based on at least one acrylic monomer and at least one acrylic polymer comprising a powder and a liquid. The powder comprises: (a) from 50 to 70 weight percent of at least one acrylic polymer having a particle size of between 20 and 150 microns; and (b) a polymerization initiator. The liquid comprises: (a) from 30 to 50 weight percent of a mixture comprising at least 65 weight percent of at least one acrylic monomer and up to 35 weight percent of at least one acrylic polymer; (b) at least one polymerization activator; and (c) from 0.05 to 1 weight percent, relative to the total amount of acrylic monomer, of at least one chain stopper chosen from the group consisting of diunsaturated monocyclic terpenes and monounsaturated bicyclic terpenes. Application to the manufacture of surgical cements.

10 Claims, No Drawings

COMPOSITIONS FOR SURGICAL CEMENT, BASED ON AT LEAST ONE ACRYLIC MONOMER AND AT LEAST ONE ACRYLIC POLYMER

BACKGROUND OF THE INVENTION

The present invention relates to compositions for surgical cement, based on at least one acrylic monomer and at least one acrylic polymer.

To obtain a surgical cement in the past, a solid phase, usually a powder consisting of polymethyl methacrylate, and a liquid syrup, consisting of a polymethyl methacrylate powder dissolved in methyl methacrylate, would be mixed and then hardened using a polymerization catalyst. The catalyst could be present in the polymethyl methacrylate powder constituting the solid phase. French Pat. No. 2,418,253, for example, describes a cement for bone surgery and stomatology, that is prepared with 35 to 70 weight percent solid acrylic polymer phase that contains a polymerization catalyst and from 30 to 65 weight percent viscous liquid phase, comprising from 15 to 35 weight percent acrylic polymer dissolved in at least 65 weight percent acrylic monomer. This cement, however, is highly exothermic when hardening, and is thus undesirable for use with sensitive tissues.

Furthermore, French Pat. No. 2,277,856 discloses a method for making a molding composition for the manufacture of dental prostheses by mixing 70 to 75 weight percent powder containing 60 to 90 weight percent polymethyl methacrylate and 10 to 40 weight percent poly-2-ethylhexyl acrylate, with 20 to 25 weight percent methyl methacrylate. Hardening takes place at 100° C. in the presence of a polymerization catalyst. The patent also teaches the addition to the mixture of an exothermic peak suppressor, which is disclosed as being 0.01 weight percent, relative to the methyl methacrylate monomer, dipentene. This composition, however, takes too long to harden and is undesirable for use in circumstances where quick setting is desired.

SUMMARY OF THE INVENTION

Among the objects of the present invention is to provide a new composition for a surgical cement with a low (less than 55° C.) temperature of polymerization so that the present invention may be used with delicate living tissues.

Another object of the present invention is to provide a composition for surgical cement with a rapid (generally less than 12 minutes) setting time.

Additional objects and advantages of the invention will be set forth in part in the description that follows, and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purposes of the invention, as embodied and broadly described herein, the invention comprises a component system for forming a surgical cement comprising a powder and a liquid. The powder comprises 50 to 70 weight percent of at least one acrylic polymer having a particle size of between 20 and 150 microns, and a polymerization initiator. The liquid comprises 30 to 50 weight percent of a mixture that comprises at least 65 weight percent of at least one acrylic monomer and up to 35 weight percent of at least one acrylic polymer; at least one polymerization activator; and from 0.05 to 1 weight percent, relative to the total amount of the acrylic monomer, of at least one chain-stopping agent chosen from the group consisting of diunsaturated monocyclic terpenes and monounsaturated bicyclic terpenes.

An "acrylic polymer" is a product obtained from homopolymerization of an acrylic monomer or copolymerization of an acrylic monomer with at least one different acrylic monomer or one comonomer such as styrene, acrylonitrile or vinyl esters like vinyl acetate. By "acrylic monomer" is meant an ester of acrylic acid or methacrylic acid with an alcohol containing 8 or fewer carbon atoms.

Reference will now be made to the presently preferred embodiment of the invention.

Methyl methacrylate may be selected as an advantageous acrylic monomer to manufacture the acrylic polymer of the powder, and as an advantageous constituent of the liquid.

The acrylic polymer in the powder may be prepared by homopolymerizing an acrylic monomer, or, if appropriate, copolymerizing the acrylic monomer in the presence of at least one other monomer, by any known means such as suspension polymerization. The acrylic polymer may also be a mixture of acrylic homopolymers or copolymers. Polymer beads obtained from suspension or another technique such as cryogenic grinding of polymer prepared by bulk polymerization, are seived to retain essentially only that fraction with a particle size between 20 and 150 microns. If particles smaller than 20 microns are not removed, too rapid thickening of the composition causes retention of occluded air and produces a heterogenous structure. If particles larger than 150 microns are not removed, the polymerization of the acrylic monomer forms an undesirable heterogenous structure because large particles are poorly soluble in acrylic monomer. The average molecular weight of the acrylic polymer is advantageously between 200,000 and 600,000.

The powder contains at least one acrylic polymer and also contains a known polymerization initiator, such as an inorganic or organic peroxide or azo-bis-isobutyronitrile (AIBN), or a photoinitiator. It is advantageous to use benzoyl peroxide, if appropriate to the cement mixture, in the form of hydrous benzoyl peroxide containing 15 to 50 weight percent water.

The initiator may be added to the acrylic polymer powder or may be present in the polymer beads if the initiator has been used in excess during the polymerization of the powder precursor.

The mixture contained in the liquid phase comprises at least 65 weight percent of at least one acrylic monomer. The mixture may comprise a single monomer or a mixture of comonomers, a polymerization activator, and at least one diunsaturated monocyclic terpene or monosaturated bicyclic terpene.

While a polymer need not be present, the mixture advantageously comprises at least one acrylic monomer and at least one acrylic polymer. The particle size of a polymer to be dissolved in the monomer is not critical, but the solution obtained should be homogeneous. The polymer used need not be the same as the polymer contained in the powder, and an advantageous average molecular weight of the polymer in the liquid is between 100,000 and 400,000.

The liquid phase may also contain a small amount of a polyunsaturated monomer (from 0.1 to 2 parts per 100 parts of acrylic monomer) that may be chosen from among the acrylic acid or methacrylic acid esters of polyols, preferably such as ethylene glycol dimethacrylate and trimethylolpropane trimethacrylate.

The polymerization activator added to the liquid phase is chosen from among products known for accelerating radical polymerizations in the presence of free radicals. A tertiary amine, preferably containing at least one aromatic nucleus, such as an N,N-dialkylaniline or N,N-dialkyl-para-toluidine, such as, for example, N,N-dimethyl-para-toluidine, is advantageous in an amount between 1 and 5 weight percent relative to the total amount of monomer contained in the liquid phase.

The chain stopping agent may be one of the diunsaturated monocyclic terpenes, such as limonene, 3,8-para-menthadiene, α-phellandrene, β-phellandrene, α-terpinene, β-terpinene, γ-terpinene, terpinolene, and isoterpinolene, and may also be monosaturated bicyclic terpenes, such as sabinene or β-pinene. Terpinolene, preferably in an amount of between 0.2 and 0.9 weight percent, relative to the total amount of acrylic monomer, is an advantageous choice for the stopping agent.

Terpene acts as a peak suppressor during the setting of the surgical cement and prevents a highly exothermic reaction from being capable of damaging delicate organic tissues that may be in contact with the cement. Terpene also acts as a chain stopper if it is present in a sufficient amount; it prevents the formation of long-chain, high molecular weight macromolecules during the polymerization of the acrylic monomer in the presence of acrylic polymer. Thus, the chain stopping agent, such as terpene, controls the setting of the surgical cement of the present invention in at least two ways so that the setting temperature does not exceed 55° C. when the powder and the liquid (usually about 70 to 80 g of total mass) are mixed at ambient temperature (about 18° to 20° C.), and when hardening takes place at the normal temperature of the human body (about 37.2° C.). Even with such a mild exothermic reaction, it is astonishing to find that the maximum degree of conversion of the monomer is reached in a remarkably short time (generally less than 12 minutes).

The activator enhances the chain-stopping function of the terpene used. Thus, starting from a given composition, it is possible to lower the maximum setting temperature reached by the mixture, either by adding more terpene or by adding more activator. Adding more of both of these constituents reduces the exothermic intensity of the polymerization even more substantially. This observation is particularly surprising insofar as the activator, used by itself, acts neither as a chain stopper nor as an exothermic peak suppressor.

Moreover, the liquid phase of the present invention may contain between 0.001 and 0.03 weight percent, relative to the total amount of acrylic monomer in the liquid, of a stabilizer. This stabilizer serves to prevent premature polymerization of the acrylic monomer. It is advantageously chosen from the group consisting of alkyl-substituted monophenols. 6-tertbutyl-2,4 dimethylphenol is a preferable example.

The powder and liquid compositions may also comprise other ingredients that have a variety of functions. The powder, for example, may contain from 30 to 50 weight percent of one or more inert fillers that may increase the compressive strength of the cement product and that may reduce shrinkage during polymerization. Fillers that may be used include: apatite—such as hydroxyapatite - silica, alumina, glass-ceramic, carbon fibers, aramide fibers, glass fibers or boron fibers, and metal fibers such as stainless steel, tantalum, or titanium fibers. An organic inert filler that is insoluble in the monomer contained in the liquid phase may also be used. An example of a filler of this type is an acrylic homopolymer or copolymer of very high average molecular weight (generally about 600,000) which is in the form of powder or beads with a particle size of between 10 and 500 microns. The presence of a filler of this type increases the mechanical strength of the cement.

The compositions of the present invention may also contain bioabsorbable fillers, for example polymers that may be resorbed in time and assimilated by the organism. An example of a filler of this type is physiological serum thickened with a polysaccharide (glucane, xanthane, or chitin), which, after resorption, leaves behind a microporous structure favoring occupation by the bone.

The powder may also contain fillers opaque to x-rays, such as barium sulfate or zirconium oxide, and colorants, for example, $Fe_2O_3$. If desired, the compositions according to the invention may also contain one or more antiseptics or alternatively one or more antibiotics, an aminoglucoside, for example.

The present invention further comprises a process for the manufacture of a surgical cement wherein a composition such as described above is poured, at a temperature of between about 10° and 30° C., into a space where a prosthesis is to be placed.

The two constituents of the composition, the powder and the liquid are mixed in proportions to give a smooth and homogeneous paste. This paste is then placed in the space created, for example, by the removal of the neck of a femur, and the prosthesis, generally made of metal, that is to replace the neck of the femur is then placed in this paste. After 8 to 10 minutes, the temperature within the surgical cement has reached 22° to 25° C., and the composition will harden in a total time of 12 to 15 minutes. Starting from the moment at which the powder and the liquid phase are mixed, a maximum temperature of 40° to 45° C. is reached.

The compositions of the invention may also be used in other applications where the maximum temperature permitted during a surgical intervention (generally 56° C.) may be exceeded. This is the case, for example, in the manufacture of dental prostheses.

The purpose of the following examples is to illustrate some embodiments of the invention without implying a limitation.

In each of the following thirty examples, the following procedure was used:

---

43 g  polymethyl methacrylate with a
      particle size of between 20 and 150 microns
5 g   zirconium oxide
0.56 g  85% strength by weight hydrous benzoyl peroxide

---

A liquid phase was prepared containing 22 g of methyl methacrylate. Terpinolene and N,N-dimethyl-para toluidine (N,N-DMPT) were added in the amounts indicated below.

At time t=0, the liquid is added to the powder at a temperature of 18° C. The two components are mixed with a spatula for 1.5 minutes, poured into a parallelpipedal mold having dimensions of 5 cm × 4.5 cm × 3.5 cm, and the maximum temperature reached by the mixture was noted.

EXAMPLES 1 and 2 (comparison)

In these examples, the liquid phase does not contain terpinolene. Rather it contains 0.33 g (Example 1) or 0.99 g (Example 2) of N,N-DMPT. The maximum temperatures reached were 101° C. (Example 1) and 98° C. (Example 2).

EXAMPLES 3 to 30

The liquid phase contains the amounts of terpinolene and N,N-DMPT indicated in Table I. The maximum temperature reached by the mixture is also indicated in Table I. The numbering of the examples in Table I is to be read from left to right.

The temperature reached by a given mixture is below that reached by a mixture containing a lower proportion of terpinolene, when the proportion of N,N-DMPT is held constant; the temperature of a given mixture is also below that reached by a mixture containing less N,N-DMPT, when the proportion of terpinolene is held constant.

Moreover, for a given proportion of terpinolene, increasing the proportion of N,N-DMPT leads to a reduction in the time taken to reach the maximum temperature, although this maximum temperature is lower. The time results are not listed, but, for example, the time taken by the mixture to reach 62.5° C. in Example 24 is 26 minutes; in Example 30, the time taken to reach 42° C. is only 16 minutes.

TABLE I

| N,N—DMPT (g) Terpinolene (g) | 0.33 | 0.44 | 0.55 | 0.66 | 0.77 | 0.88 | 0.99 | Examples |
|---|---|---|---|---|---|---|---|---|
| 0.05 | 88° C. | 86° C. | 82° C. | 78° C. | 76° C. | 74.5° C. | 72° C. | 3 to 9 |
| 0.10 | 79° C. | 78° C. | 71° C. | 70° C. | 66° C. | 64° C. | 63° C. | 10 to 16 |
| 0.15 | 72.5° C. | 69° C. | 63° C. | 62.5° C. | 56° C. | 54° C. | 53° C. | 17 to 23 |
| 0.20 | 62.5° C. | 59° C. | 56° C. | 54° C. | 52° C. | 48° C. | 42° C. | 24 to 30 |

TABLE II

| N,N—DMPT (g) Terpinolene (g) | 0.44 | 0.66 | 0.88 | 1.10 | Examples |
|---|---|---|---|---|---|
| 0.05 | 48.0° C. | 46.0° C. | 44.7° C. | 43.3° C. | 31 to 34 |
| 0.10 | 44.3° C. | 43.1° C. | 42.8° C. | 41.0° C. | 35 to 38 |
| 0.20 | 42.0° C. | 41.5° C. | 41.3° C. | 40.5° C. | 39 to 42 |

EXAMPLES 31 to 42

The powder and the liquid phase are prepared as in Examples 1 to 30 and mixed as in Examples 1 to 30 and poured into a mold after 3.5 minutes. After standing for one minute, the mold is immersed in a thermostatically controlled chamber containing physiological serum kept at a temperature of 37.2° C. The maximum temperature reached in the mold during the polymerization is recorded.

The mold used had an internal structure and a thickness conforming to French Standard Specification S 90 430. The mold consists of a cylindrical polytetrafluoroethylene shell with an external diameter of 90 mm, an internal diameter of 60 mm and a thickness of 6 mm, provided with a V-shaped notch for filling and an orifice for insertion of the temperature-measuring probe. The shell is held by means of screw clamps between two aluminum cheeks with a diameter of 90 mm and a thickness of 1.5 mm, coated with a 50 micron layer of polytetrafluoroethylene.

Table II shows the temperature reached for differing proportions of terpinolene and N,N-DMPT. The highest temperatures are reached in shorter time with a high proportion of N,N-DMPT, but the time dependence on the proportion of N,N-DMPT is not appreciable. The times range from 13 to 11 minutes after immersion of the mold into the thermostatically controlled bath.

EXAMPLE 43 (comparison)

Using the same measurement conditions as in Examples 31 to 42, a component system without terpinolene was tested. The powder was prepared as follows:

| | |
|---|---|
| 46.95 g | Copolymer of methyl methacrylate (90%) and of butyl methacrylate (10%) |
| 0.12 g | 85% strength by weight hydrous benzoyl peroxide |

The liquid phase was prepared as follows:

| | |
|---|---|
| 17.58 g | methyl methacrylate |
| 1.95 g | butyl methacrylate |
| 0.4 g | N,N—DMPT |

The maximum temperature observed in the mixture of the powder and the liquid was 65.2° C.

EXAMPLE 44

Under the same conditions as in Example 43, a liquid phase was prepared that also contained 0.07 g of terpinolene.

The maximum temperature reached was 46.1° C.

EXAMPLE 45 (comparison)

A composition was prepared as follows:

Powder:
- 43 g polymethyl methacrylate
- 5 g ZrO$_2$
- 0.56 g 85% strength by weight hydrous benzoyl peroxide Liquid:
- 21.8 g Methyl methacrylate
- 0.2 g trimethylolpropane trimethacrylate
- 0.48 g N,N—DMPT Using the same measuring conditions as in Examples 31 to 42, the maximum temperature reached after mixing was 63.4° C.

EXAMPLE 46 (comparison)

A composition was prepared as follows:

Powder:
- 39.53 g polymethyl methacrylate
- 0.47 g 85% strength hydrous benzoyl peroxide Liquid:
- 8 g polymethyl methacrylate -continued 18.6 g methyl methacrylate
0.4 g N,N—DMPT Using the same measuring conditions as in Examples 31 to 42, the maximum temperature reached after mixing was 65.5° C.

EXAMPLE 47

Terpinolene (0.12 g) is added to a liquid prepared as in Example 45. The maximum temperature reached was 44° C.

EXAMPLE 48

A composition was prepared as follows:

Powder:
42.7 g polymethyl methacrylate
4.75 g $ZnO_2$
0.56 g 85% strength hydrous benzoyl peroxide Liquid:
7.2 g polymethyl methacrylate
22.8 g methyl methacrylate
0.06 g terpinolene
0.55 g N,N—DMPT
0.006 g 6-tertbutyl-2,4-dimethylphenol Using the measuring conditions used in Examples 1 to 30, the maximum temperature reached was 47° C. Under the same measuring conditions, the composition described in Example 46, prepared without terpinolene, resulted in a maximum temperature of 70° C.

It will be apparent to those skilled in the art that various modifications and variations could be made in the composition of the invention without departing from the scope or spirit of the invention.

What is claimed is:

1. A component system for forming a surgical cement comprising a powder and a liquid, wherein said powder comprises:
   (a) 50 to 70 weight percent of at least one acrylic polymer having a particle size of between 20 and 150 microns; and
   (b) a polymerization initiator,
and wherein said liquid comprises:
   (a) 30 to 50 weight percent of a mixture comprising at least 65 weight percent of at least one acrylic monomer and up to 35 weight percent of at least one acrylic polymer;
   (b) at least one polymerization activator; and
   (c) from 0.05 to 1 weight percent, relative to the total amount of said acrylic monomer in said liquid, of at least one chain stopping agent chosen from the group consisting of diunsaturated monocyclic terpenes and monounsaturated bicyclic terpenes.

2. The component system of claim 1, wherein said polymerization activator comprises 1 to 5 weight percent, relative to the total amount of said acrylic monomer in said liquid, of said liquid.

3. The component system of claim 1, wherein said polymerization activator is N,N-dimethyl-para-toluidene.

4. The component system of claim 1, wherein said chain stopping agent is terpinolene.

5. The component system of claim 1, wherein said polymerization activator is N,N-dimethyl-para-toluidene and said chain stopping agent is terpinolene.

6. The component system of claim 1, wherein said liquid further comprises from 0.001 to 0.03 weight percent, relative to the total amount of said acrylic monomer in said liquid, of a stabilizer.

7. The component system of claim 6, wherein said stabilizer is selected from the group consisting of alkyl-substituted monophenols.

8. The component system of claim 7, wherein said stabilizer is 6-tertbutyl-2,4,-dimethylphenol.

9. A component system for forming a surgical cement comprising a powder and a liquid, wherein said powder comprises:
   (a) 50 to 70 weight percent of at least one acrylic polymer having a particle size of between 20 and 150 microns; and
   (b) a polymerization initiator,
and wherein said liquid comprises:
   (a) 30 to 50 weight percent of a mixture comprising at least one acrylic monomer and up to 35 weight percent of at least one acrylic polymer;
   (b) 1 to 5 weight percent, relative to the total amount of said acrylic monomer in said liquid, of N,N-dimethyl-para-toluidene;
   (c) from 0.05 to 1 weight percent, relative to the total amount of said acrylic monomer, of terpinolene; and
   (d) from 0.001 to 0.03 weight percent, relative to the total amount of said acrylic monomer in said liquid, of 6-tertbutyl-2,4,-dimethylphenol.

10. A process for the manufacture of a surgical cement, wherein the component system of claim 1 is poured, at a temperature of between about 10° and 30° C. into a space where a prosthesis is to be placed.

* * * * *